US006146635A

United States Patent [19]

Cano et al.

[11] Patent Number: 6,146,635

[45] Date of Patent: Nov. 14, 2000

[54] SYSTEM FOR THE EXPRESSION OF HETEROLOGOUS ANTIGENS AS FUSION PROTEINS

[75] Inventors: Carlos Antonio Durate Cano; Enrique Gerardo Guillen Nieto; Anabel Alvarez Acosta, all of Habana; Luis Emilio Carpio Munoz, Sancti Spiritus; Diogenes Quintana Vazquez, Pinar del Rio; Carmen Elena Gomez Rodriquez, Habana; Recardo de la Caridid Siva Rodriguez, Habana; Consuelo Nazabal Galvez, Habana; Maria De Jesus Leal Angulo, Habana; Alejandro Miguel Martin Dunn, Habana, all of Cuba

[73] Assignee: Centro de Ingenieria Genetica Y Biotecnologia, Havana, Cuba

[21] Appl. No.: 08/930,917

[22] PCT Filed: Jan. 17, 1997

[86] PCT No.: PCT/CU97/00001

§ 371 Date: Sep. 16, 1997

§ 102(e) Date: Sep. 16, 1997

[87] PCT Pub. No.: WO97/26359

PCT Pub. Date: Jul. 24, 1997

[30] Foreign Application Priority Data

Jan. 17, 1996 [CU] Cuba .......................................... 10/96

[51] Int. Cl.[7] ......................... A61K 39/00; A61K 39/02; A61K 39/21; A61K 39/095

[52] U.S. Cl. .................................... 424/192.1; 424/185.1; 424/190.1; 424/208.1; 424/250.1; 424/249.1; 424/184.1; 530/350; 530/825; 530/820

[58] Field of Search ............................. 424/185.1, 184.1, 424/208.1, 192.1, 249.1, 250.1; 530/350, 820, 825, 864; 435/252.3, 252.33

[56] References Cited

U.S. PATENT DOCUMENTS 5,286,484 2/1994 Rodriguez et al. ................ 435/252.33

FOREIGN PATENT DOCUMENTS 0 474 313 A2 3/1992 European Pat. Off. .
WO 90/14431 11/1990 WIPO .

OTHER PUBLICATIONS

Niebla et al. In: Neisseria 94, Proceedings of the Ninth International Pathogenic Neisseria Conference, (Ed) Evans et al. Winchester, England, Sep. 26–30, 1994.

Guillen et al. Biotechnol. Apl. 12: 72, 1995.

Guillen et al. Biotechnol. Apl. 13: 271–275, 1996.

*Primary Examiner*—James C. Housel
*Assistant Examiner*—S. Devi
*Attorney, Agent, or Firm*—Lackenbach Siegel Marzullo Aronson & Greenspan P.C.

[57] ABSTRACT

The present invention relates to biotechnology and genetic engineering, particularly the expression of proteins of viral origin in microorganisms through their fusion, by applying the recombinant DNA technology, to bacterial peptides. The present invention provides an efficient process for the expression in *Escherichia coli* of heterologous proteins as fusion polypeptides with a view to obtaining them with a high degree of purity, in commercially useful amounts, and in an appropriate form for their inclusion in vaccine preparations intended to human use. To this effect, what is essentially used is a stabilizing sequence derived from the first 47 amino acids of the antigen P64k of *Neisseria meningitidis* B:4:P1.15. In particular, use is made of a recombinant plasmid containing said sequence, under the control of the tryptophane promotor of *E. coli* and of the terminator of the transcription of the phage T4, including restriction sites which provide for the cloning in phase of DNA fragments coding for polypeptides of interest. The process of the invention is applicable to the pharmaceutical industry, for the development of diagnostic systems, vaccine preparations, and in any situation where it is required to obtain high amounts of heterologous proteins as fusion polypeptides in *E. coli.*

13 Claims, 12 Drawing Sheets

FIG. 1

10 20 30 40 50 60 70
*ATGCTAGATA AAAGA*ATGGC TTTAGTTGAA TTGAAAGTGC CCGACATTGG CGGACACGAA AATGTAGATA
80 90 100 110 120 130 140
TTATCGCGGT TGAAGTAAAC GTGGGCGACA CTATTGCTGT GGACGATACC CTGATTACTT TGGAAACCGA
150 160 170 180 190 200 210
TAAAGCGACT ATGGACGTAC CTGCTGAAGT TGCAGGCGTA GTCAAAGAAG TTAAAGTTAA AGTCGGCGAC
220 230 240 250 260 270 280
AAAATCTCTG AAGGTGGTTT GATTGTCGTC GTTGAAGCTG AAGGCACGGC AGCCGCTCCT AAAGCCGAAG
290 300 310 320 330 340 350
CGGCTGCCGC CCCGGCGCAA GAAGCCCCTA AAGCTGCCGC TCCTGCTCCG CAAGCCGCGC AATTCGGCGG
360 370 380 390 400 410 420
TTCTGCCGAT GCCGAGTACG ACGTGGTCGT ATTGGGTGGC GGTCCCGGCG GTTACTCCGC TGCATTTGCC
430 440 450 460 470 480 490
GCTGCCGATG AAGGCTTGAA AGTCGCCATC GTCGAACGTT ACAAAACTTT GGGCGGCGTT TGCCTGAACG
500 510 520 530 540 550 560
TCGGCTGTAT CCCTTCCAAA GCCTTGTTGC ACAATGCCGC CGTTATCGAC GAAGTGCGCC ACTTGGCTGC
570 580 590 600 610 620 630
CAACGGTATC AAATACCCCG AGCCGGAACT CGACATCGAT ATGCTTCGCG CCTACAAAGA CGGCGTAGTT
640 650 660 670 680 690 700
TCCCGCCTCA CGGGCGGTTT GGCAGGTATG GCGAAAAGCC GTAAAGTGGA CGTTATCCAA GGCGACGGGC
710 720 730 740 750 760 770
AATTCTTAGA TCCGCACCAC TTGGAAGTGT CGCTGACTGC CGGCGACGCG TACGAACAGG CAGCCCCTAC
780 790 800 810 820 830 840
CGGCGAGAAA AAAATCGTTG CCTTCAAAAA CTGTATCATT GCAGCAGGCA GCCGCGTAAC CAAACTGCCT
850 860 870 880 890 900 910
TTCATTCCTG AAGATCCGCA CATCATCGAT TCCAGCGGCG CATTGGCTCT GAAAGAAGTA CCGGGCAAAC
920 930 940 950 960 970 980
TGCTGATTAT CGGCGGCGGC ATTATCAGCC TCGAGATGGG TACGGTTTAC AGCACGCTGG GTTCGCGTTT
990 1000 1010 1020 1030 1040 1050
GGATGTGGTT GAAATGATGG ACGGCCTGAT GCAAGGCGCA GACCGCGATT TGGTAAAAGT ATGGCAAAAA
1060 1070 1080 1090 1100 1110 1120
CAAAACGAAT ACCGTTTTGA CAACATTATG GTCAACACCA AAACCGTTGC AGTTGAGCCG AAAGAAGACG
1130 1140 1150 1160 1170 1180 1190
GCGTTTACGT TACCTTTGAA GGCGCGAACG CGCCTAAAGA GCCGCAACGC TACGATGCCG TATTGGTTGC
1200 1210 1220 1230 1240 1250 1260
CGCCGGCCGC GCGCCCAACG GCAAACTCAT CAGCGCGGAA AAAGCAGGCG TTGCCGTAAC CGATCGCGGC
1270 1280 1290 1300 1310 1320 1330
TTCATCGAAG TGGACAAACA AATGCGTACC AATGTGCCGC ACATCTACGC CATCGGCGAC ATCGTCGGTC
1340 1350 1360 1370 1380 1390 1400
AGCCGATGTT GGCGCACAAA GCCGTTCACG AAGGCCACGT TGCCGCCGAA AACTGCGCCG GCCACAAAGC
1410 1420 1430 1440 1450 1460 1470
CTACTTCGAC GCACGCGTGA TTCCGGGCGT TGCCTACACT TCCCCCGAAG TGGCGTGGGT GGGCGAAACC
1480 1490 1500 1510 1520 1530 1540
GAACTGTCCG CCAAAGCCTC CGGCCGCAAA ATCACCAAAG CCAACTTCCC GTGGGCGGCT TCCGGCCGTG
1550 1560 1570 1580 1590 1600 1610
CGATTGCCAA CGGTTGCGAC AACGGCTTTA CCAAGCTGAT TTTTGATGCC GAAACCGGCC GCATCATCGG
1620 1630 1640 1650 1660 1670 1680
CGGCGGCATT GTCGGTCCGA ACGGTGGCGA TATGATCGGC GAAGTCTGCC TTGCCATCGA AATGGGCTGC
1690 1700 1710 1720 1730 1740 1750
GACGCGGCAG ACATCGGCAA AACCATCCAC CCGCACCCGA CCTTGGGCGA ATCCATCGGT ATGGCGGCGG
1760 1770 1780 1790 1797
AAGTGGCATT GGGTACTTGT ACCGACCTGC CTCCGCAAAA GAAAAAA

FIG. 3

```
                                                                    4
                                                               5' TTCC

                      16        25        34        43        52
M   V   D   K   R   M   A   L   V   E   L   K   V   P   D   I   G   G   H
ATG GTA GAT AAA AGA ATG GCT TTA GTT GAA TTG AAA GTG CCC GAC ATT GGC GGA CAC

    61            70        79        88        97        106       115
E   N   V   D   I   I   A   V   E   V   N   V   G   D   T   I   A   V   D
GAA AAT GTA GAT ATT ATC GCG GTT GAA GTA AAC GTG GGC GAC ACT ATT GCT GTG GAC

        124       133       142
D   T   L   I   T   L   D   L   E
GAT ACC CTG ATT ACT TTG GAT CTA GAA A  3'
```

FIG. 5

| Seqences producing High-scoring Segment Pairs: | High Score | Smallest Poisson Probability P(N) | N |
|---|---|---|---|
| KPY1_HUMAN PYRUVATE KINASE, M1 (MUSCLE) ISOZYME (EC 2.7.1... | 51 | 0.98 | 1 |
| KPY1_RAT PYRUVATE KINAZE, M1 (MUSCLE) ISOZYME (EC 2.7.1... | 51 | 0.98 | 1 |
| KPY2_HUMAN PYRUVATE KINAZE, M2 ISOZYME (EC 2.7.1.40). | 51 | 0.98 | 1 |
| KPY2_RAT PYRUVATE KINAZE, M2 ISOZYME (EC 2.7.1.40). | 51 | 0.98 | 1 |

```
>KPY1_HUMAN PYRUVATE KINASE, M1 (MUSCLE) ISOZYME (EC 2.7.1.40) (CYTOSOLIC
            THYROID HORMONE-BINDING PROTEIN)
            Length = 530

Query:   29 VNVGDTIAVDDTLITLDL 46
            V+VG  I VDD  LI+L++
Sbjct:  167 VEVGSKIYVDDGLISLQV 184

>KPY1_RAT PYRUVATE KINASE, M1 (MUSCLE) ISOZYME (EC 2.7.1.40).
          Length = 530

Query:   29 VNVGDTIAVDDTLITLDL 46
            V+VG  I VDD  LI+L++
Sbjct:  167 VEVGSKIYVDDGLISLQV 184

>KPY2_HUMAN PYRUVATE KINASE, M2 ISOZYME (EC 2.7.1.40).
            Length = 530

Query:   29 VNVGDTIAVDDTLITLDL 46
            V+VG  I VDD  LI+L++
Sbjct:  167 VEVGSKIYVDDGLISLQV 184

>KPY2_RAT PYRUVATE KINASE, M2 ISOZYME (EC 2.7.1.40).
          Length = 530

Query:   29 VNVGDTIAVDDTLITLDL 46
            V+VG  I VDD  LI+L++
Sbjct:  167 VEVGSKIYVDDGLISLQV 184
```

FIG. 6

| Seqences producing High-scoring Segment Pairs: | | Reading Frame | High Score | Smallest Poisson Probability P(N) | N |
|---|---|---|---|---|---|
| CFMUCIN | Canis familiaris (clone pCTM-A) mucin c-term... | -2 | 62 | 0.30 | 1 |
| HS8671 | EST02755 Homo sapiens cDNA clone HFBCA72 sim... | -2 | 61 | 0.40 | 1 |

>CFMUCIN Canis familiaris (clone pCTM-A) mucin c-terminus RNA, 3' end.
Length = 1733

```
Query:     8 LVELKVPDIGGHENVDIIAVEVNVGDTIAVDD 39
             L E+ VPD   H  V+++A  E+ +G+++   VDD
Sbjct:  1015 LREVQVPDRKLHKGVQLLAGELGIGEALQVDD 920
```

>HS8671 EST02755 Homo sapiens cDNA clone HFBCA72 similar to Mucin CTM-A.
Length = 286

```
Query:     8 LVELKVPDIGGHENVDIIAVEVNVGDTIAVDD 39
             L E+ VPD   HE V++++ E+ VG    VDD
Sbjct:   240 LREVQVPDRKLHEGVQLLSGELGVGKXFQVDD 145
```

FIG. 8

12 21 30 39 48 57
M V D K R M A L V E L K V P D I G G H
ATG GTA GAT AAA AGA ATG GCT TTA GTT GAA TTG AAA GTG CCC GAC ATT GGC GGA CAC
69 78 87 96 105 114
E N V D I I A V E V N V G D T I A V D
AA AAT GTA GAT ATT ATC GCG GTT GAA GTA AAC GTG GGC GAC ACT ATT GCT GTG GAC
126 135 144 153 162 171
D T L I T L D L D S R G I R I G P G R
GAT ACC CTG ATT ACT TTG GAT CTA GAC TCG AGA GGC ATT CGT ATC GGC CCA GGT CGC
183 192 201 210 219 228
A I L A T A G G G A R Q S T P I G L G
GCA ATT TTA GCA ACA GCT GGC GGT GGC GCA CGT CAA TCT ACC CCT ATT GGT TTA GGT
240 249 258 267 276 285
G A L Y T T A G G G A R K S I T K G P
CAG GCT CTG TAT ACG ACT GCC GGC GGT GGT GCG CGC AAA AGT ATC ACC AAG GGT CCA
297 306 315 324 333 342
G R V I Y A T A G G G A R K R I H I G
GGC CGC GTC ATT TAC GCC ACC GCG GGC GGC GGT GCC CGT AAG CGT ATC CAC ATT GGC
354 363 372 381 390 399
P G R A F Y T T A G G G A R K R I T M
CCA GGC CGT GCA TTC TAT ACT ACA GCA GGT GGT GGC GCA CGT AAA CGC ATC ACT ATG
411 420 429 438 447 456
G P G R V Y Y T T A G G G A S I R I Q
GGT CCT GGT CGC GTC TAT TAC ACG ACC GCT GGC GGC GGT GCT AGC ATT CGC ATC CAA
468 477 486 495
R G P G R A F V T I *
CGC GGC CCT GGT CGT GCA TTT GTG ACC ATA TGA

FIG. 10A
| Gene | Stabilizer | Plasmid | Culture medium | % of expression |
|---|---|---|---|---|
| *porA* | hIL2-58 | pILM-28 | M9 | 32 |
| | P64k-47 | pM-82 | M9 | 34 |
| *opc* | hIL2-58 | pILM-29 | M9 | 25 |
| | P64k-47 | pM-80 | M9 | 20 |
| TAB | hIL2-22 | pTAB4 | LB | 5 |
| | P64k-47 | pTAB4 | LB | 10 |
FIG. 10B
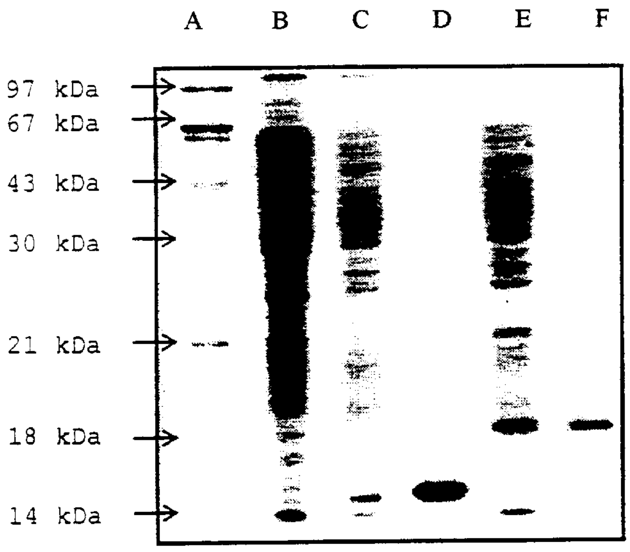
FIG. 10C
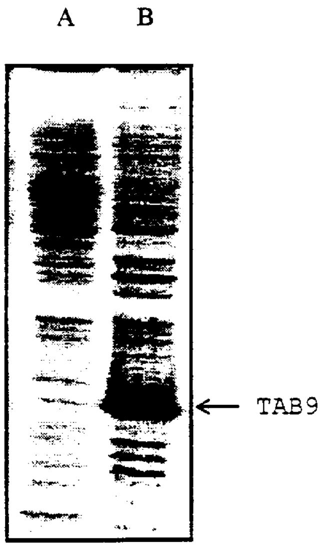

FIG. 12

| | TAB 4 | | | | TAB 9 | | | |
|---|---|---|---|---|---|---|---|---|
| RABBIT# | 12166 | 5725 | 5340 | 2310 | 1 | 2 | 3 | 10 |
| TAB | 20480 | 10240 | 10240 | 81920 | 20480 | 20480 | 51200 | 51200 |
| | 0 | 0 | 0 | 0 | 0 | 0 | | |
| LR150 | <100 | <100 | <100 | 6400 | 400 | <100 | 800 | <100 |
| JY1 | 200 | <100 | <100 | 12800 | 1600 | 6400 | 3200 | <100 |
| RF | 6400 | <100 | 3200 | 800 | <100 | 200 | 3200 | 800 |
| MN | 200 | <100 | <100 | 1600 | 1600 | 3200 | 6400 | <100 |
| BRVA | <100 | 6400 | 400 | 3200 | 800 | 400 | 6400 | 1600 |
| IIIB | <100 | <100 | <100 | <100 | 800 | <100 | 800 | <100 |
| GM | 1820 | | | | 1416 | | | |
| R% | 45.8% | | | | 75% | | | |

SEQUENCE LISTING (1) GENERAL INFORMATION:

(iii) NUMBER OF SEQUENCES: 21

(2) INFORMATION FOR SEQ ID NO: 1:

(i) SEQUENCE CHARACTERISTICS:
(A) LENGTH: 47 Amino acid residues
(B) TYPE: Amino acid
(C) STRANDEDNESS: Unknown
(D) TOPOLOGY: Unknown (ii) MOLECULE TYPE: Peptide (iii) HYPOTHETICAL: No (iv) ANTI-SENSE: No (v) FRAGMENT TYPE: -N Terminal fragment (vi) ORIGINAL SOURCE:
(A) ORGANISM: Neisseria meningitidis
(B) STRAIN: B:4:P1.15

(vii) IMMEDIATE SOURCE:
(A) LIBRARY: Genomic
(B) CLONE: P64K (ix) FEATURE:
(D) OTHER INFORMATION: First 47 amino acids of the recombinant protein of Neisseria meningitidis P64K.

(xi) SEQUENCE DESCRIPTION: SEQ ID NO: 1:

```
Met Leu Asp Lys Arg Met Ala Leu Val Glu Leu Lys Val Pro Asp Ile
1               5                   10                  15

Gly Gly His Glu Asn Val Asp Ile Ile Ala Val Glu Val Asn Val Gly
            20                  25                  30

Asp Thr Ile Ala Val Asp Asp Thr Leu Ile Thr Leu Glu Thr Asp
        35                  40                  45
```

(2) INFORMATION FOR SEQ ID NO: 2:

(i) SEQUENCE CHARACTERISTICS:
(A) LENGTH: 29 base pairs
(B) TYPE: Nucleic acid
(C) STRANDEDNESS: Unknown
(D) TOPOLOGY: Unknown (ii) MOLECULE TYPE: Other nucleic acid
(A) DESCRIPTION: Synthetic oligonucleotide (iii) HYPOTHETICAL: No.

(iv) ANTI-SENSE: No (v) FRAGMENT TYPE: -N Terminal fragment (vi) ORIGINAL SOURCE:
(A) ORGANISM: Neisseria meningitidis
(B) STRAIN: B:4:P1.15

(vii) IMMEDIATE SOURCE:
(A) LIBRARY: Genomic
(B) CLONE: P64K (ix) FEATURE:
(A) NAME/KEY: 1573
(D) OTHER INFORMATION: Primer 5' for PCR amplification of the first 44 amino acids of the recombinant protein of Neisseria meningitidis P64K.

-continued (xi) SEQUENCE DESCRIPTION: SEQ ID NO: 2:

TTCCATGGTA GATAAAAGAA TGGCTTTAG 29

(2) INFORMATION FOR SEQ ID NO:3:

(i) SEQUENCE CHARACTERISTICS:
(A) LENGTH: 29 base pairs
(B) TYPE: Nucleic acid
(C) STRANDEDNESS: Unknown
(D) TOPOLOGY: Unknown (ii) MOLECULE TYPE: Other nucleic acid
(A) DESCRIPTION: Synthetic oligonucleotide (iii) HYPOTHETICAL: No.

(iv) ANTI-SENSE: No (v) FRAGMENT TYPE: -C Terminal fragment (vi) ORIGINAL SOURCE:
(A) ORGANISM: Neisseria meningitidis
(B) STRAIN: B:4:P1.15

(vii) IMMEDIATE SOURCE:
(A) LIBRARY: Genomic
(B) CLONE: P64K (ix) FEATURE:
(A) NAME/KEY: 1575
(D) OTHER INFORMATION: Primer 3' for PCR amplification of the first 47 amino acids of the recombinant protein of Neisseria meningitidis P64K.

(xi) SEQUENCE DESCRIPTION: SEQ ID NO: 3:

TTTCTAGATC CAAAGTAATC AGGGTATCG 29

(2) INFORMATION FOR SEQ ID NO:4:

(i) SEQUENCE CHARACTERISTICS:
(A) LENGTH: 26 base pairs
(B) TYPE: Nucleic acid
(C) STRANDEDNESS: Unknown
(D) TOPOLOGY: Unknown (ii) MOLECULE TYPE: Other nucleic acid
(A) DESCRIPTION: Synthetic oligonucleotide (iii) HYPOTHETICAL: No (iv) ANTI-SENSE: No (v) FRAGMENT TYPE: -C Terminal fragment (vi) ORIGINAL SOURCE:
(A) ORGANISM: Neisseria meningitidis
(B) STRAIN: B:4:P1.15

(vii) IMMEDIATE SOURCE:
(A) LIBRARY: Genomic
(B) CLONE: P64K (ix) FEATURE:
(A) NAME/KEY: Primer 2192
(D) OTHER INFORMATION: Primer 3' for PCR amplification of the first 120 amino acids of the recombinant protein of Neisseria meningitidis P64K (xi) SEQUENCE DESCRIPTION: SEQ ID NO: 4:

GGCGGTTCTG CCGATTAAGG ATCCGA 26

(2) INFORMATION FOR SEQ ID NO:5:

-continued (i) SEQUENCE CHARACTERISTICS:
(A) LENGTH: 146 base pairs
(B) TYPE: Nucleic acid
(C) STRANDEDNESS: Unknown
(D) TOPOLOGY: Unknown (ii) MOLECULE TYPE: Other nucleic acid
(A) DESCRIPTION: Fragment amplified by PCR (iii) HYPOTHETICAL: Yes (iv) ANTI-SENSE: No (v) FRAGMENT TYPE: -N-terminal fragment (vi) ORIGINAL SOURCE:
(A) ORGANISM: Neisseria meningitidis
(B) STRAIN: B:4:P1.15

(vii) IMMEDIATE SOURCE:
(A) LIBRARY: Genomic
(B) CLONE: P64K (ix) FEATURE:
(D) OTHER INFORMATION: Fragment derived from the first 47 amino acids of the recombinant protein of Neisseria meningitidis P64K, containing a NcoI site at the position 3 to 8 and a XbaI site at the position 139 to 144

(xi) SEQUENCE DESCRIPTION: SEQ ID NO: 5:

```
TTCCATGGTA GATAAAAGAA TGGCTTTAGT TGAATTGAAA GTGCCCGACA TTGGC          60

CGAAAATGTA GATATTATCG CGGTTGAAGT AAACGTGGGC GACACTATTG CTGTG         120

TACCCTGATT ACTTTGGATC TAGAAA                                         146
```

(2) INFORMATION FOR SEQ ID NO: 6:

(i) SEQUENCE CHARACTERISTICS:
(A) LENGTH: 47 Amino acid residues
(B) TYPE: Amino acid
(C) STRANDEDNESS: Unknown
(D) TOPOLOGY: Unknown (ii) MOLECULE TYPE: Peptide (iii) HYPOTHETICAL: No (iv) ANTI-SENSE: No (v) FRAGMENT TYPE: -N Terminal fragment (vi) ORIGINAL SOURCE:
(A) ORGANISM: Neisseria meningitidis
(B) STRAIN: B:4:P1.15

(vii) IMMEDIATE SOURCE:
(A) LIBRARY: Genomic
(B) CLONE: P64K (ix) FEATURE:
(D) OTHER INFORMATION: Stabilizer derived from the first 47 amino acids of the recombinant protein of Neisseria meningitidis P64K, containing the following changes: L2 V2; E45 D45;T46 L46; D47 E47.

(xi) SEQUENCE DESCRIPTION: SEQ ID NO: 6:

```
Met Val Asp Lys Arg Met Ala Leu Val Glu Leu Lys Val Pro Asp Ile
1               5                   10                  15

Gly Gly His Glu Asn Val Asp Ile Ile Ala Val Glu Val Asn Val Gly
            20                  25                  30

Asp Thr Ile Ala Val Asp Asp Thr Leu Ile Thr Leu Asp Leu Glu
        35                  40                  45
```

-continued (2) INFORMATION FOR SEQ ID NO: 7:

(i) SEQUENCE CHARACTERISTICS:
(A) LENGTH: 16 base pairs
(B) TYPE: Nucleic acid
(C) STRANDEDNESS: Unknown
(D) TOPOLOGY: Unknown (ii) MOLECULE TYPE: Other nucleic acid
(A) DESCRIPTION: Synthetic oligonucleotide (iii) HYPOTHETICAL: No.

(iv) ANTI-SENSE: No (v) FRAGMENT TYPE: -N Terminal fragment (vi) ORIGINAL SOURCE:
(A) ORGANISM: Neisseria meningitidis
(B) STRAIN: B:4:P1.15

(vii) IMMEDIATE SOURCE:
(A) LIBRARY: Genomic
(B) CLONE: P64K (ix) FEATURE:
(A) NAME/KEY: 1576

(xi) SEQUENCE DESCRIPTION: SEQ ID NO:7 :

CTAGATTTGA TATCAG 16

(2) INFORMATION FOR SEQ ID NO: 8:

(i) SEQUENCE CHARACTERISTICS:
(A) LENGTH: 16 base pairs
(B) TYPE: Nucleic acid
(C) STRANDEDNESS: Unknown
(D) TOPOLOGY: Unknown (ii) MOLECULE TYPE: Other nucleic acid
(A) DESCRIPTION: Synthetic oligonucleotide (iii) HYPOTHETICAL: No (iv) ANTI-SENSE: No (v) FRAGMENT TYPE: -N Terminal fragment (vi) ORIGINAL SOURCE:
(A) ORGANISM: Neisseria meningitidis
(B) STRAIN: B:4:P1.15

(vii) IMMEDIATE SOURCE:
(A) LIBRARY: Genomic
(B) CLONE: P64K (ix) FEATURE:
(A) NAME/KEY: 1577

(xi) SEQUENCE DESCRIPTION: SEQ ID NO: 8 :

GATCCTGATA TCAAAT 16

(2) INFORMATION FOR SEQ ID NO: 9:

(i) SEQUENCE CHARACTERISTICS:
(A) LENGTH: 15 Amino acid residues
(B) TYPE: Amino acid
(C) STRANDEDNESS: Unknown
(D) TOPOLOGY: Unknown (ii) MOLECULE TYPE: Peptide (iii) HYPOTHETICAL: No -continued (iv) ANTI-SENSE: No (v) FRAGMENT TYPE: Internal fragment (vi) ORIGINAL SOURCE:
(A) ORGANISM: VIH-1
(C) INDIVIDUAL ISOLATE: LR150

(ix) FEATURE:
(D) OTHER INFORMATION: Central region of the loop V3 belonging to the protein gp120 from the VIH-1, isolation LR150

(xi) SEQUENCE DESCRIPTION: SEQ ID NO: 9:

```
Ser Arg Gly Ile Arg Ile Gly Pro Gly Arg Ala Ile Leu Ala Thr
1               5                   10                  15
```

(2) INFORMATION FOR SEQ ID NO: 10:

(i) SEQUENCE CHARACTERISTICS:
(A) LENGTH: 15 Amino acid residues
(B) TYPE: Amino acid
(C) STRANDEDNESS: Unknown
(D) TOPOLOGY: Unknown (ii) MOLECULE TYPE: Peptide (iii) HYPOTHETICAL: No (iv) ANTI-SENSE: No (v) FRAGMENT TYPE: Internal fragment (vi) ORIGINAL SOURCE:
(A) ORGANISM: VIH-1
(C) INDIVIDUAL ISOLATE: JY1

(ix) FEATURE:
(D) OTHER INFORMATION: Central region of the loop V3 belonging to the protein gp120 from the VIH-1, isolation JY1.

(xi) SEQUENCE DESCRIPTION: SEQ ID NO: 10:

```
Arg Gln Ser Thr Pro Ile Gly Leu Gly Gln Ala Leu Tyr Thr Thr
1               5                   10                  15
```

(2) INFORMATION FOR SEQ ID NO: 11:

(i) SEQUENCE CHARACTERISTICS:
(A) LENGTH: 15 Amino acid residues
(B) TYPE: Amino acid
(C) STRANDEDNESS: Unknown
(D) TOPOLOGY: Unknown (ii) MOLECULE TYPE: Peptide (iii) HYPOTHETICAL: No (iv) ANTI-SENSE: No (v) FRAGMENT TYPE: Internal fragment (vi) ORIGINAL SOURCE:
(A) ORGANISM: VIH-1
(C) INDIVIDUAL ISOLATE: RF (ix) FEATURE:
(D) OTHER INFORMATION: Central region of the loop V3 belonging to the protein gp120 from the VIH-1, isolation RF (xi) SEQUENCE DESCRIPTION: SEQ ID NO: 11:

```
Arg Lys Ser Ile Thr Lys Gly Pro Gly Arg Val Ile Tyr Ala Thr
1               5                   10                  15
```

-continued (2) INFORMATION FOR SEQ ID NO: 12:

(i) SEQUENCE CHARACTERISTICS:
(A) LENGTH: 15 Amino acid residues.
(B) TYPE: Amino acid.
(C) STRANDEDNESS: Unknown.
(D) TOPOLOGY: Unknown.

(ii) MOLECULE TYPE: Peptide (iii) HYPOTHETICAL: No (iv) ANTI-SENSE: No (v) FRAGMENT TYPE: Internal fragment (vi) ORIGINAL SOURCE:
(A) ORGANISM: VIH-1
(C) INDIVIDUAL ISOLATE: MN (ix) FEATURE:
(D) OTHER INFORMATION: Central region of the loop V3 belonging to the protein gp120 from the VIH-1, isolation MN.

(xi) SEQUENCE DESCRIPTION: SEQ ID NO: 12:

```
Arg Lys Arg Ile His Ile Gly Pro Gly Arg Ala Phe Tyr Thr Thr
1               5                   10                  15
```

(2) INFORMATION FOR SEQ ID NO: 13:

(i) SEQUENCE CHARACTERISTICS:
(A) LENGTH: 15 Amino acid residues
(B) TYPE: Amino acid
(C) STRANDEDNESS: Unknown
(D) TOPOLOGY: Unknown (ii) MOLECULE TYPE: Peptide (iii) HYPOTHETICAL: No (iv) ANTI-SENSE: No (v) FRAGMENT TYPE: Internal fragment (vi) ORIGINAL SOURCE:
(A) ORGANISM: VIH-1
(C) INDIVIDUAL ISOLATE: BRVA (ix) FEATURE:
(D) OTHER INFORMATION: Central region of the loop V3 belonging to the protein gp120 from the VIH-1, isolation BRVA.

(xi) SEQUENCE DESCRIPTION: SEQ ID NO: 13:

```
Arg Lys Arg Ile Thr Met Gly Pro Gly Arg Val Tyr Tyr Thr Thr
1               5                   10                  15
```

(2) INFORMATION FOR SEQ ID NO: 14:

(i) SEQUENCE CHARACTERISTICS:
(A) LENGTH: 15 Amino acid residues
(B) TYPE: Amino acid
(C) STRANDEDNESS: Unknown
(D) TOPOLOGY: Unknown (ii) MOLECULE TYPE: Peptide (iii) HYPOTHETICAL: No (iv) ANTI-SENSE: No (v) FRAGMENT TYPE: Internal fragment -continued (vi) ORIGINAL SOURCE:
(A) ORGANISM: VIH-1
(C) INDIVIDUAL ISOLATE: IIIB (ix) FEATURE:
(D) OTHER INFORMATION: Central region of the loop V3 belonging to the protein gp120 from the VIH-1, isolation IIIB.

(xi) SEQUENCE DESCRIPTION: SEQ ID NO: 14:

```
Ser Ile Arg Ile Gln Arg Gly Pro Gly Arg Ala Phe Val Thr Ile
1               5                   10                  15
```

(2) INFORMATION FOR SEQ ID NO:15:

(i) SEQUENCE CHARACTERISTICS:
(A) LENGTH: 15 Amino acid residues.
(B) TYPE: Amino acid.
(C) STRANDEDNESS: Unknown.
(D) TOPOLOGY: Unknown.

(ii) MOLECULE TYPE: Peptide (iii) HYPOTHETICAL: Yes (iv) ANTI-SENSE: No (v) FRAGMENT TYPE: Internal fragment (vi) ORIGINAL SOURCE:
(A) ORGANISM: VIH-1

(ix) FEATURE:
(D) OTHER INFORMATION: Consensus sequence of the central region of the loop V3 belonging to the protein gp120 obtained from different isolations of the VIH-1, position 7 within the multiepitopic polypeptide (MEP) TAB13.

(xi) SEQUENCE DESCRIPTION: SEQ ID NO: 15:

```
Thr Ser Ile Thr Ile Gly Pro Gly Gln Val Phe Tyr Arg Thr Gly
1               5                   10                  15
```

(2) INFORMATION FOR SEQ ID NO: 16:

(i) SEQUENCE CHARACTERISTICS:
(A) LENGTH: 15 Amino acid residues
(B) TYPE: Amino acid
(C) STRANDEDNESS: Unknown
(D) TOPOLOGY: Unknown (ii) MOLECULE TYPE: Peptide (iii) HYPOTHETICAL: Yes (iv) ANTI-SENSE: No (v) FRAGMENT TYPE: Internal fragment (vi) ORIGINAL SOURCE:
(A) ORGANISM: VIH-1

(ix) FEATURE:
(D) OTHER INFORMATION: Consensus sequence of the central region of the loop V3 belonging to the protein gp120 obtained from different isolations of the VIH-1, position 8 within the multiepitopic polypeptide (MEP) TAB13.

(xi) SEQUENCE DESCRIPTION: SEQ ID NO: 16:

```
Arg Gln Arg Thr Ser Ile Gly Gln Gly Gln Arg Leu Tyr Thr Thr
1               5                   10                  15
```

-continued (2) INFORMATION FOR SEQ ID NO: 17:

(i) SEQUENCE CHARACTERISTICS:
(A) LENGTH: 5 Amino acid residues
(B) TYPE: Amino acid
(C) STRANDEDNESS: Unknown
(D) TOPOLOGY: Unknown (ii) MOLECULE TYPE: Peptide (iii) HYPOTHETICAL: No (iv) ANTI-SENSE: No (v) FRAGMENT TYPE: Internal fragment (ix) FEATURE:
(D) OTHER INFORMATION: Flexible spacer separating epitopes V3 in the MEP TAB3, TAB4, TAB9 and TAB13.

(xi) SEQUENCE DESCRIPTION: SEQ ID NO: 17:

```
Ala Gly Gly Gly Ala
1               5
```

(2) INFORMATION FOR SEQ ID NO: 18:

(i) SEQUENCE CHARACTERISTICS:
(A) LENGTH: 141 Amino acid residues
(B) TYPE: Amino acid
(C) STRANDEDNESS: Unknown
(D) TOPOLOGY: Unknown (ii) MOLECULE TYPE: Peptide (iii) HYPOTHETICAL: No (iv) ANTI-SENSE: No (v) FRAGMENT TYPE: Internal fragment (vi) ORIGINAL SOURCE:
(A) ORGANISM: VIH-1

(ix) FEATURE:
(D) OTHER INFORMATION: Multiepitopic polypeptide (MEP) TAB4.

(xi) SEQUENCE DESCRIPTION: SEQ ID NO: 18:

```
Met Ala Pro Thr Ser Ser Ser Thr Ala Gln Thr Gln Leu Gln Leu Glu
1               5                   10                  15

His Leu Leu Leu Asp Leu Gln Ile Phe Leu Ser Arg Gly Ile Arg Ile
            20                  25                  30

Gly Pro Gly Arg Ala Ile Leu Ala Thr Ala Gly Gly Gly Ala Arg Gln
        35                  40                  45

Ser Thr Pro Ile Gly Leu Gly Gly Ala Leu Tyr Thr Thr Ala Gly Gly
    50                  55                  60

Gly Ala Arg Lys Ser Ile Thr Lys Gly Pro Gly Arg Val Ile Tyr Ala
65                  70                  75                  80

Thr Ala Gly Gly Gly Ala Arg Lys Arg Ile His Ile Gly Pro Gly Arg
                85                  90                  95

Ala Phe Tyr Thr Thr Ala Gly Gly Gly Ala Arg Lys Arg Ile Thr Met
            100                 105                 110

Gly Pro Gly Arg Val Tyr Tyr Thr Thr Ala Gly Gly Gly Ala Ser Ile
        115                 120                 125

Arg Ile Gln Arg Gly Pro Gly Arg Ala Phe Val Thr Ile
    130                 135                 140
```

(2) INFORMATION FOR SEQ ID NO: 19:

-continued (i) SEQUENCE CHARACTERISTICS:
(A) LENGTH: 162 Amino acid residues
(B) TYPE: Amino acid
(C) STRANDEDNESS: Unknown
(D) TOPOLOGY: Unknown (ii) MOLECULE TYPE: Peptide (iii) HYPOTHETICAL: No (iv) ANTI-SENSE: No (v) FRAGMENT TYPE: Internal fragment (vi) ORIGINAL SOURCE:
(A) ORGANISM: VIH-1

(ix) FEATURE:
(D) OTHER INFORMATION: Multiepitopic polypeptide (MEP) TAB9.

(xi) SEQUENCE DESCRIPTION: SEQ ID NO: 19:

```
Met Val Asp Lys Arg Met Ala Leu Val Glu Leu Lys Val Pro Asp Ile
1               5                   10                  15

Gly Gly His Glu Asn Val Asp Ile Ile Ala Val Glu Val Asn Val Gly
            20                  25                  30

Asp Thr Ile Ala Val Asp Asp Thr Leu Ile Thr Leu Asp Leu Asp Ser
        35                  40                  45

Arg Gly Ile Arg Ile Gly Pro Gly Arg Ala Ile Leu Ala Thr Ala Gly
    50                  55                  60

Gly Gly Ala Arg Gln Ser Thr Pro Ile Gly Leu Gly Gly Ala Leu Tyr
65                  70                  75                  80

Thr Thr Ala Gly Gly Gly Ala Arg Lys Ser Ile Thr Lys Gly Pro Gly
                85                  90                  95

Arg Val Ile Tyr Ala Thr Ala Gly Gly Gly Ala Arg Lys Arg Ile His
            100                 105                 110

Ile Gly Pro Gly Arg Ala Phe Tyr Thr Thr Ala Gly Gly Gly Ala Arg
        115                 120                 125

Lys Arg Ile Thr Met Gly Pro Gly Arg Val Tyr Tyr Thr Thr Ala Gly
    130                 135                 140

Gly Gly Ala Ser Ile Arg Ile Gln Arg Gly Pro Gly Arg Ala Phe Val
145                 150                 155                 160

Thr Ile
```

(2) INFORMATION FOR SEQ ID NO: 20:

(i) SEQUENCE CHARACTERISTICS:
(A) LENGTH: 202 Amino acid residues
(B) TYPE: Amino acid
(C) STRANDEDNESS: Unknown
(D) TOPOLOGY: Unknown (ii) MOLECULE TYPE: Peptide (iii) HYPOTHETICAL: No (iv) ANTI-SENSE: No (v) FRAGMENT TYPE: Internal fragment.

(vi) ORIGINAL SOURCE:
(A) ORGANISM: VIH-1

(ix) FEATURE:
(D) OTHER INFORMATION: Multiepitopic polypeptide (MEP) TAB13.

(xi) SEQUENCE DESCRIPTION: SEQ ID NO: 20:

-continued

```
Met Val Asp Lys Arg Met Ala Leu Val Glu Leu Lys Val Pro Asp Ile
1               5                   10                  15

Gly Gly His Glu Asn Val Asp Ile Ile Ala Val Glu Val Asn Val Gly
            20                  25                  30

Asp Thr Ile Ala Val Asp Asp Thr Leu Ile Thr Leu Asp Leu Asp Ser
        35                  40                  45

Arg Gly Ile Arg Ile Gly Pro Gly Arg Ala Ile Leu Ala Thr Ala Gly
    50                  55                  60

Gly Gly Ala Arg Gln Ser Thr Pro Ile Gly Leu Gly Gln Ala Leu Tyr
65                  70                  75                  80

Thr Thr Ala Gly Gly Gly Ala Arg Lys Ser Ile Thr Lys Gly Pro Gly
                85                  90                  95

Arg Val Ile Tyr Ala Thr Ala Gly Gly Gly Ala Arg Lys Arg Ile His
            100                 105                 110

Ile Gly Pro Gly Arg Ala Phe Tyr Thr Thr Ala Gly Gly Gly Ala Arg
        115                 120                 125

Lys Arg Ile Thr Met Gly Pro Gly Arg Val Tyr Tyr Thr Thr Ala Gly
    130                 135                 140

Gly Gly Ala Arg Gln Arg Thr Ser Ile Gly Gln Gly Gln Ala Leu Tyr
145                 150                 155                 160

Thr Thr Ala Gly Gly Gly Ala Thr Ser Ile Thr Ile Gly Pro Gly Gln
                165                 170                 175

Val Phe Tyr Arg Thr Gly Ala Gly Gly Gly Ala Ser Ile Arg Ile Gln
            180                 185                 190

Arg Gly Pro Gly Arg Ala Phe Val Thr Ile
        195                 200
```

(2) INFORMATION FOR SEQ ID NO: 21:

(i) SEQUENCE CHARACTERISTICS:
(A) LENGTH: 368 base pairs
(B) TYPE: Nucleic acid
(C) STRANDEDNESS: Unknown
(D) TOPOLOGY: Unknown (ii) MOLECULE TYPE: Other nucleic acid
(A) DESCRIPTION: Synthetic oligonucleotide (iii) HYPOTHETICAL: No (iv) ANTI-SENSE: No (v) FRAGMENT TYPE: Internal fragment (vi) ORIGINAL SOURCE:
(A) ORGANISM: VIH-1

-continued

```
(ix) FEATURE:
      (D) OTHER INFORMATION: Codifies for epitopes V3 linked
           by the spacer of SEQ ID NO: 17: in the MEP TAB 19.

(xi) SEQUENCE DESCRIPTION: SEQ ID NO: 21:

TCTAGACTCG AGAGGCATTC GTATCGGCCC AGGTCGCGCA ATTTTAGCAA CAGCTGGCGG     60

TGGCGCACGT CAATCTACCC CTATTGGTTT AGGTCAGGCT CTGTATACGA CTGCCGGCGG    120

TGGTGCGCGC AAAAGTATCA CCAAGGGTCC AGGCCGCGTC ATTTACGCCA CCGCGGGCGG    180

CGGTGCCCGT AAGCGTATCC ACATTGGCCC AGGCCGTGCA TTCTATACTA CAGCAGGTGG    240

TGGCGCACGT AAACGCATCA CTATGGGTCC TGGTCGCGTC TATTACACGA CCGCTGGCGG    300

CGGTGCTAGC ATTCGCATCC AACGCGGCCC TGGTCGTGCA TTTGTGACCA TATGATAACG    360

CGGGATCC                                                             368
```

SYSTEM FOR THE EXPRESSION OF HETEROLOGOUS ANTIGENS AS FUSION PROTEINS

This application is the national stage filing under 35 U.S.C. § 371 of PCT/CU97/00001 (WO 97/26359), filed Jan. 17, 1997 and claims priority benefit of Cuban Patent Application No. 10/96, filed Jan. 17, 1996.

TECHNICAL SECTOR

The present invention is related to the field of the Biotechnology and the genetic engineering, particularly to the expression of heterologous proteins in microbial hosts through their fusion to bacteria peptides, using the technology of the recombinant DNA.

PREVIOUS ART

The usefulness of the technology of the recombinant DNA to produce proteins of any origin in *E. coli* has been extensively demonstrated. For this, an important amount of vectors have been developed, although new variants are necessary due to the fact that, frequently each gene to clone and to express represents an individual case (Denhardt, D. T. and Colasanti, J.; Vectors ed., Butterworths, Stoneham, MA, Biotechnology 10, 179–203, 1988 and Lukacsovich, T. et al., Journal of Biotechnology, 13, 243–250, 1990).

The intracellular synthesis has been the most used strategy for the obtainment of heterologous polypeptides in *E. coli,* due to the high expression levels reachable (Goeddel, D. V, Methods Enzymol., 185, 3–7, 1990). However, factors such as the sensitivity to proteases of the host or toxicity of the expressed protein can reduce significantly said levels, independently of the use of regulatory sequences of high efficiency (Lee, C. A. and Saier, M. H., J. Bacteriol., 153, 685–692, 1983; Gwyn, G. W., Membrane Protein Expression Systems: A User's Guide, Portland Press, London, UK, 29–82, 1992). The cloning of nucleotide sequences encoding for proteins of interest in suitable vectors, in frame with sequences of nucleic acid that encode stable polypeptides in the host cell, gives rise to the expression of hybrid products in the cytoplasm, known as fusion proteins (Marston, F. A. O., Biochem. J. 240, 1–12, 1986). Such polypeptides are generally less sensitive to proteolytic degradation by the host or less toxic due to the formation of inclusion bodies, which results in higher expression levels to those obtained without the use of the stabilizer peptide (Itakura, K. et al., Science, 198, 1056–1063, 1977). In addition, this kind of expression facilitates and cheapens the initial steps of the purification if different methods for the subsequent renaturation of the recombinant product are available (Fischer, B., Sumner, I. and Goodenough, P., Biotechnol. Bioeng., 41, 3–13, 1993).

The inclusion bodies are insoluble protein aggregates that appear as electrodense bodies in the cytosol during the expression of many recombinant proteins in *E. coli* (Rinas, U. and Bailey, J., Appl. Microbiol. Biotechnol., 37, 609–614, 1992). They are the result of the interaction between polypeptides partially folded, whose aggregation is thermodynamically favored due to the exposition, within them, of hydrophobic residues to the solvent (Kiefhaber, T., Rudolph, R. et al., Biotechnology, 9, 825–829, 1991). The slow folding in the bacterial cytosol of many eukaryotic proteins, due to the abundance of disulfide bridges-forming amino acids (Cysteino) or beta-turn-forming amino acids (Proline) has stimulated the abundant use of them as stabilizer peptides. Examples of the former are the use, with this purpose, of polypeptides with binding activity to antibodies, coming from the globulin of the fat of the human milk (HMFG), according to the international patent application PCT No. WO 9207939 A2 920514; from constant regions of the immunoglobulins, as described in the European patent application No. EP 0464533 A1 920108; from the human angiogenin (European patent application No. EP 0423641 A2 910424), of the growth hormone (EP 0429586 A1 910605), the glutatione-S-tranferase (WO 8809372 A1 881201) and of the swine adenylate quinase (EP 0423641 A2 910424 and EP 0412526 A2 910213).

However, the use of stabilizer polypeptides that constitute a significant part of the fusion protein has some disadvantages if the former is a vaccine candidate, since the presence of the foreign sequences can alter the natural order of the B and T cell epitopes (Denton, G., Hudecz, F., Kajtár, J. et al., Peptide Research, 7, 258–264, 1994) or the processing of the same by the antigen presenting cells (Del Val, M., Schlicht, H., Ruppert, T., et al, Cell, 66, 1145–1153, 1991), being able to even affect seriously the immunogenicity of the candidate by the phenomenon of specific-epitope suppression (Etlinger, H., Immunol. Today, 13, 52–55, 1992).

As a result of the aforementioned phenomenon, in some cases, small fragments that still stabilize the expression have been tried to be defined. For example, the German patent application No. 35 41 856 A1 (Hoechst AG) reports the possibility of using a stabilizer peptide conformed by at least the first 95 amino acids of the N-terminus of the human protein Interleukine (IL-2) to obtain fusion proteins in an insoluble form synthesized in *E. coli.* Similarly in the European Patent Applications No. 0 416 673 A2 and No. 229 998 from the same company, a stabilizer peptide consistent in the first 58 or 38 amino acids of said protein, is used. In the European patent No. 416 673 B1, the first 58 amino acids of the IL-2 are also used, and a similar strategy is followed, with this purpose, in the case of use of N-terminal fragments of the human seroalbumin (European patent application No. EP 0423641 A1 920212); the activator peptide III of the connective tissue (WO 90136647 A1 901115) and fragments of the human kallikrein (EP 0381433 A1 900808). These inventions give solution to the previous problem, but the fusion polypeptides obtained can not be included in vaccine preparations for use in humans, due to the possibility of induction of autoimmune diseases for the presence in them of homologous or identical sequences to human proteins.

The alternative of using stabilizer polypeptides of bacterial origin—and therefore, without cross reactivity with antigens of human origin—for intracellular expression, has also been explored with success. One of the most used proteins with this end has been the β-galactosidase of *E. coli* (Itakura, K. et al., Science, 198, 1056–1063, 1977) or portions of it (German patent application No. EP 0235754 A2 870909, of the company Hoechst AG). The principal disadvantage of this system is the great size of this protein which provokes that the desired peptide only represents a small portion of the total hybrid protein (Flores, N. et al., Appl. Microbiol. Biotechnol. 25, 267–271, 1986; Goeddel, D. V. et al., P.N.A.S. USA, 76, 106–110, 1979). Similar problems are presented with the use of the C fragment of the tetanus toxoid and the exotoxin of Pseudomonas sp. (International Patent Application PCT WO 9403615 A1 940217 and European Patent Application EP 0369316 A2 900523). An expression variant that is very promising is the use of fusions with the thioredoxin of *E. coli* (PCT Patent application No. WO 9402502 A1 940203), that uses the property of being liberated from the cell by osmotic stress (el Yasgoubi, A., Kohiyama, M., Richarme, G., J. Bacteriol., 176, 7074–7078, 1994) to facilitate the purification. However, this outline is not functional for the obtainment of inclusion bodies, since the same are not freed through this procedure.

Many of these problems have been solved with the design of modular fusion proteins. In these, the stabilizer peptide is separated from the protein of interest by a spacer that permits the independent folding of both, and whose amino acid sequence makes it susceptible to the attack of specific endopeptidases. If there is a ligand that recognizes the chosen stabilizer, it is possible to purify the fusion polypeptide by affinity chromatography and finally separate it from the stabilizer through the treatment with different proteases (Cress, D., Shultz, J. and Breitlow, S., Promega Notes, 42, 2–7, 1993). An additional advantage is the possibility of exploiting this molecular interaction for the follow-up of intermediate steps of the purification, without the need of antibodies for each protein to express. A well-known example of that is the use of the affinity of histidine (Hys) with some metals like nickel (Ni) and zinc (Zn) in systems composed of a stabilizer with 6 His in tandem and an affinity matrix of nickel chelates, according to what is described in the PCT Patent application No. WO 9115589 A1 911017 of The Upjohn Co. In spite of all this, this kind of expression system does not function in all the cases, since, among other reasons, the protein of interest can have restriction sites for the chosen protease, or be folded so that the spacer is available to the solvent (Uhlen, M. and Moks, T., Meth. Enzymol. 185, 129–143, 1990; Cress, D., Shultz, J. and Breitlow, S., Promega Notes, 42, 2–7, 1993), to interfere with the binding between the stabilizer and the affinity matrix (New England Biolabs, The NEB Transcript, 3, 1, 1991), or simply to require, for its purification, conditions that affect its biological activity. For these reasons it is desirable to have different variants, since each protein to express can represent a particular case. With this purpose, there have been developed stabilizer peptides based on the maltose binding protein of *E. coli* (MalE), which have affinity for the amylose resins (European Patent Application EP 0426787 A1 910515); in the chloramphenicol acetyl transferase enzymes (European Patent Application No. EP 0131363 A1 850116) or in the glutatione-S-transferase (European Patent Application No. EP 0293249 A1 88130, of the Amrad Corp., Ltd.) obtainable with matrixes of immobilized substrate; in the protein A of *Staphylococcus aureus,* according to the patent application PCT WO 9109946 A1 910711; and in the 12.5 kDa subunit of the transcarboxylase complex of *Proprionibacterium shermanii,* which is biotinylated in vivo and permits the purification based on the affinity of the biotin to avidin (Cress, D., Shultz, J. and Breitlow, S., Promega Notes, 42, 2–7, 1993; patent applications No. EP 0472658 A1 920304 or WO 9014431 A1 901129).

Of particular interest is the method described in the European Patent Application EP 0472658 A1 920304 or WO 9014431 A1 901129, developed by Biotechnology Research and Development Corporation, along with the University of Illinois, USA. In this application an expression system is described that uses the lipoic acid binding domain of the dihydrolipoamida acetyltransferese (EC 2.3.1.12), also known as the E2 subunit of the pyrovate dehydrogenase complex of *E. coli.* This domain is modified postranslationally in vivo by the addition of a lipoic acid molecule to the nitrogen of one of its lysines (Guest, J. R., Angier, J. S. and Russell, G. C., Ann. N.Y. Acad. Sci., 573, 76–99, 1989), which is exploited for the purification and identification of fused proteins through the use of an antibody that recognizes only lipoylate domains.

This method, however, has a number of drawbacks. First of all, it is known that the over expression of proteins containing binding domains to the lipoic acid exceeds the capacity of cellular lipoylation, producing as a consequence no lipoylates domains (miles, J. S. and Guest, J. R., Biochem. J., 245, 869–874, 1987 ; Ali, S. T. and Guest, J. R., Biochem. J., 271, 139–145) or octanoilates (Ali, S. T., Moir, A. J., Ashton, P. R. et al. Mol. Microbiol., 4, 943–950, 1990; Dardel, F., Packman, L. C. and Perham, R. N., FEBS Lett. 264, 206–210, 1990, which can reduce the yield during purification by immunoaffinity. In second place, there are a group of diseases of a supposed autoimmune origin which have as a common factor the presence of antibodies that recognize specifically the lipoic acid in the context of these domains. Among them are primary biliary cirrhosis, a chronic disease characterized by the inflammation and progressive obstruction of the intrahepatic bile ducts (Tuaillon, N., Andre, C., Briand, J. P. et al., J. Immunol., 148, 445–450, 1992); and hepatitis and the hepatitis provoked by halothane, an anesthetic of wide use that derivatizes some proteins by the formation of trifluoroacetyl lysine (Gut, J., Christen, U., Frey, N. et al, Toxicology, 97, 199–224, 1995). The serum of the patients with this disease recognizes said complexes, whose molecular structure is mimicked by the lipoic acid in the context of the dihydrolipoamide acetyl transferases (Gut, J., Christen, U., Frey, N. et al., Toxicology, 97, 199–224, 1995). For this reason it is desirable to avoid the presence of the lipoic acid in such peptides if the fusion proteins that contain it constitute vaccine candidates for use in humans.

DISCLOSURE OF THE INVENTION

An object of the present invention is a procedure for the expression to high levels of heterologous proteins as fusion polypeptides in *E. coli,* which is based on the use of a stabilizer sequence derivative from the first 47 amino acids of the P64K antigen of *N. meningitidis* B:4:P1.15 (European Patent application No. 0 474 313 A2) that confers on them the capacity of being expressed as inclusion bodies. Said sequence, though presents homology with part of the lipoic acid binding domain of the dihydrolipoamide acetyl transferases, has been genetically manipulated to eliminate the possibility of modification for itself and presents the advantage of being lowly immunogenic. This procedure also includes the use of a monoclonal antibody that specifically recognizes the mentioned stabilizer, permitting the immunodetection of any protein fused to the same.

Particularly, in the present invention, a recombinant plasmid as an expression vector is used which carries said sequence under the control of the tryptophan promoter (ptrip) of *E. coli,* followed by restriction sites XbaI, EcoRV and BamHI. These permit the in frame cloning of DNA fragments encoding for polypeptides of interest. This vector also includes a terminator of the transcription of the gene 32 of bacteriophage T4 and a resistance gene to ampicillin as selection marker.

This procedure makes possible also the inclusion of the fusion polypeptide obtained in vaccine preparations destined to be used in humans; and the nature of the stabilizer peptide employed permits the generation of protective immune response against the foreign protein or the multiepitopic peptide bound to it.

A novelty of the present invention is the genetic manipulation and the use of an homologous stabilizer peptide to part of the lipoic acid binding domain of the dihydrolipoamide acetyl transferases, for the production of fusion proteins by recombinant DNA technology in *E. coli.* Particularly, novelties of the present invention are the use, with the previous objective, of a stabilizer peptide derivative of the first 47 amino acids of the P64K antigen of *N. meningitidis* B:4:P1.15 (European Patent application No. 0 474 313 A2), and a monoclonal antibody that specifically recognizes the stabilizer.

The values obtained (FIG. 12) show that the titers against the V3 regions are similar between the varying IL2-22+MEP (TAB4) and P64K-47+MEP (TAB9). Though the recognition frequency of the peptides is slightly greater for the TAB9, this difference is not meaningful statistically ($p<0.05$). In conclusion, the immunogenicity of the heterologous protein is affected by the stabilizer P64K-47 in a minimal way, and comparable to other expression systems currently in use.

DESCRIPTION OF THE FIGURES

FIG. 1: Nucleotide sequence of the gene lpdA gene coding for P64K. It is shown in italic the sequence added in the plasmid pM-6 (European Patent application No. 0 474 313 A2), absent originally in the gene lpdA.

FIG. 3: Amino acid sequence of the stabilizer, deduced of the DNA sequence amplified by PCR from plasmid pM-6. The underlined sequences correspond to the oligonucleotide primers.

FIG. 5: Results of the search of homology between the sequences of the stabilizer ('Query') and those present in the SWISS-PROT ('Sbjct') base, using the BLASTP program. The corresponding income for human proteins or for mammals proteins are only shown. P(N) represents the probability of finding N equal alignments within a base composed of random sequences; the significance of the homology diminishes with the value of P(N). Identical residues are represented with their codes of one letter; the conservatives substitutions with a '+', and the differences are not indicated.

FIG. 6: Results of the search of homology between the sequences of the stabilizer ('Query') and all the possible translations of the sequences of the EMBL Data Library ('Sbjct'), using the program TBLASTN. The corresponding income to human proteins or mammal proteins are only shown. P(N) represents the probability of finding N equal alignments within a base composed of random sequences; the significance of the homology diminishes with the value of P(N). Identical residues are represented with their code of one letter; the conservative substitutions with a '+', and the differences are not indicated.

FIG. 8: Nucleotide and amino acid sequences of the MEP TAB9.

FIG. 10: Comparison of the expression of the genes porA, opc and the MEP under stabilizer derivatives from the human IL-2 or from the first 47 amino acids of the P64K antigen.

A: Comparative table. hIL2-58 refers to the first 58 amino acids of the human IL-2, hIL2-22 to the first 22, and P64K-47 to stabilizer derivative from the first 47 amino acids of the P64K antigen.

B: Comparative analysis by SDS-PAGE of the expression of the MEP in the plasmids TAB4 and TAB9. Lane A: Molecular weight markers; B: Total proteins of the strain W3110 LrpA905; C: Total proteins of W3110 trpA905+pTAB4; D: Purified TAB4; E: Total proteins of W3110 LrpA905 pTAB9; F: Purified TAB9.

C: Expression of TAB9 in inclusion bodies. A: Soluble proteins of the sample. B: Insoluble proteins or of membrane.

Figure 11:
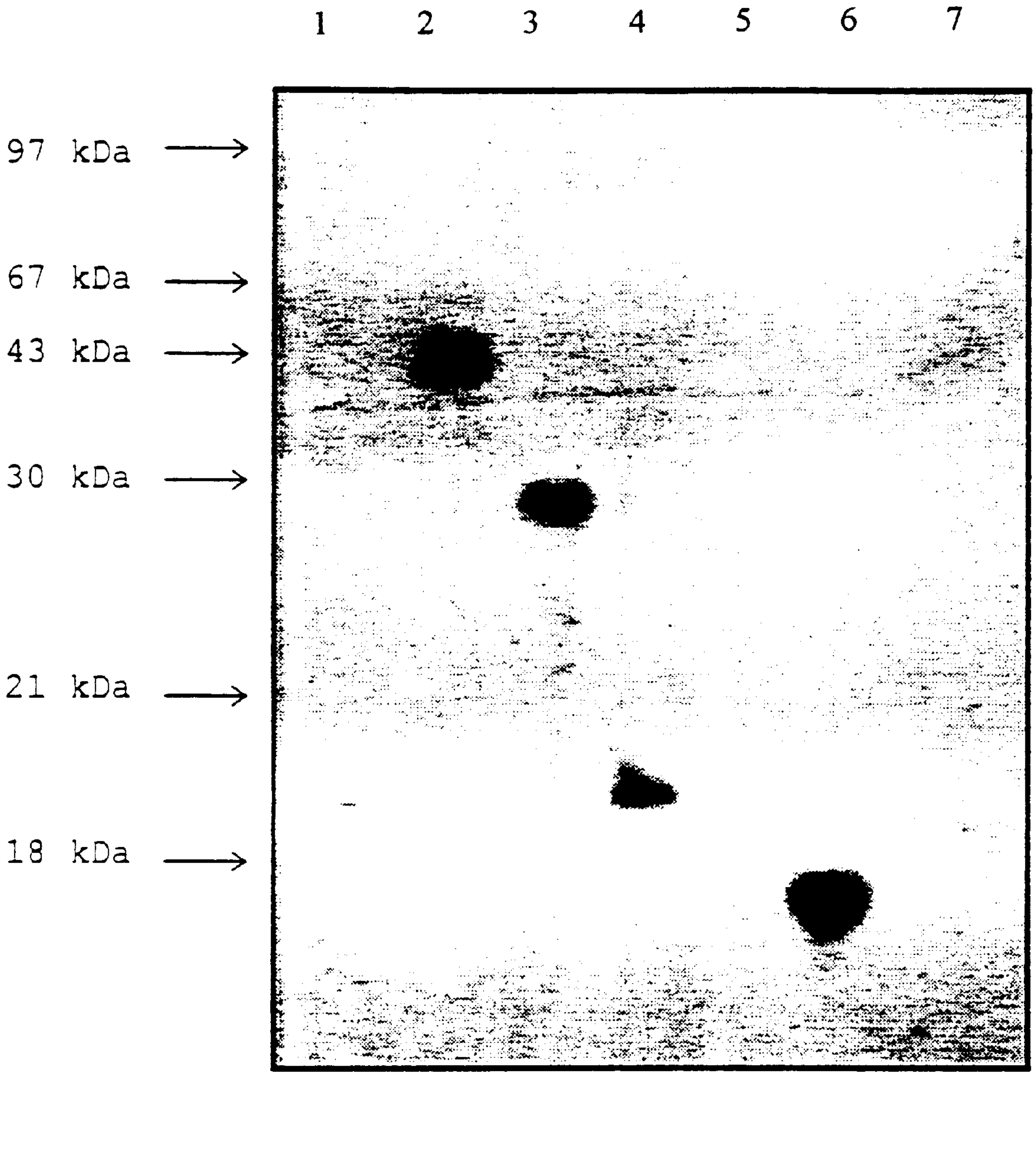

FIG. 11: Western blotting using MAb 448/30/7 with total protein samples of *E. coli* MM294 transformed with: 1: Negative control, 2: pM-6 (P64K), 3: pM-82 (P64K-47+porA), 4: pTAB13 (P64K-47+MEP), 5: pFP15 (IL-2), 6: pM-134 (P64K-120), 7: pILM-28 (IL2-58+porA) . The molecular weight markers are indicated on the left.

FIG. 12: Reciprocal of the titer value by ELISA of the rabbits immunized with TAB4 and TAB9. GM: Geometric mean of the reciprocal of the titers anti V3; R: Percent of reactivity with the V3 peptides.

EXAMPLES

Example 1

The LpdA antigen of *N. meningitidis* (P64K, LpdA) is a protein of 594 amino acids that belongs to the family of the dihydrolipoamide dehydrogenases (EC 1.8.1.4) and specifically, to a new subgroup within them, characterized by possessing a lipoic acid binding domain, analogous to the one present in the dihydrolipoamide acetyltransferases, in its N-terminal portion (Kruger, N., Oppermann, F. B., Lorenzl, H. and Steinbüchel, A., J. Bacteriol., 176, 3614–3630,1994; Hein, S. and Steinbüchel, A., J. Bacteriol., 176, 4394–4408, 1994). The LpdA protein has been cloned and over expressed in *E. coli,* with the addition of 5 amino acids (MLDKR) in its N-terminal end (European Patent application No. 0 474 313 A2; FIG. 1). Although the denominations LpdA and P64K are equivalent, the name P64K for referring to the recombinant protein will be used.

In order to determine the immunogenicity of different fragments from said antigen and to analyze the possibility of using the less immunogenic as stabilizer peptide, the epitopes for B cells present in P64K were located through the evaluation of the reactivity of a polyclonal serum anti-P64k against synthetic peptides.

With this aim, the P64K protein was purified (European Patent application No. 0 474 313 A2) through hydrophoficity chromatography of n-Betyl-TSK and gel-filtration; and it was denatured by precipitation with trichloroacetic acid (TCA) neutralizing them with NaOH and balancing in phosphate buffer by gel-filtration chromatography. This preparation was used to immunize 30 mice Balb/c by subcutaneous route with doses of 20 $^{\mu}$g adsorbed to 2 $^{\mu}$g of aluminum hydroxide adjurant (day 0), which were then boosted with the same antigen 7 and 21 days later. Sera were collected 28 days after the first extraction. The sera obtained were combined, and the resulting mixture was aliquoted and stored at −20° C.

Furthermore, 59 peptides of 20 amino acids (a.a.) each covering the entire sequence of the recombinant protein and overlapped by 10 a.a., were synthesized using a commercial kit for the synthesis in solid phase (Multipin Peptide Synthesis System, Chairon Mimotope Pty., Ltd., USA) in 96 wells—plates format and following the instructions given by the manufacturer. These were subsequently numbered from the N-terminal end of the protein. The reactivity of the serum antiP64k against these peptides was determined using a dilution 1:2000 of the same, and the format of immunoassay used was the same as one recommended by the manufacturer of the previous commercial kit.

Figure 2:
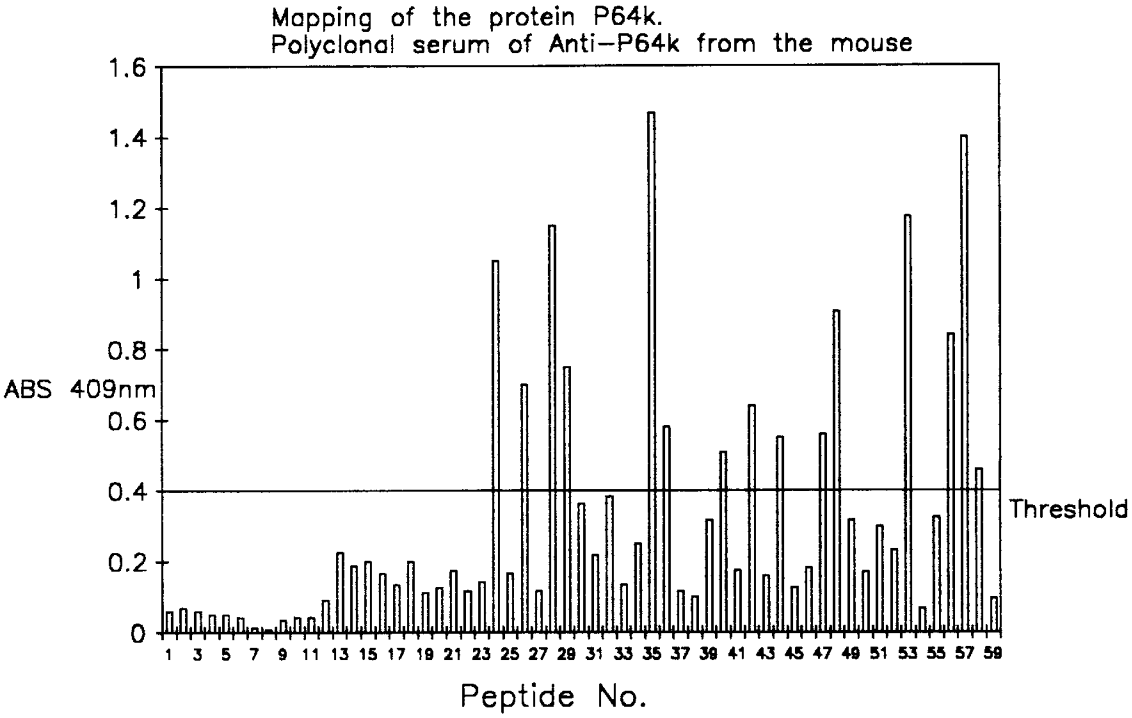
FIG. 2: Reactivity of the polyclonal serum of mouse against peptides of the P64K. A minimal value of 0.4 optical density units to consider the result as positive was chosen.

The results are shown in the FIG. 2, in which absorbance values for each peptide are represented. It is evident that the first 110 amino acids (represented by the peptides 1 to 11) form a poorly immunogenic segment in spite of the denaturation of the immunogen, which can even expose cryptic epitopes. This segment includes essentially the lipoic acid binding domain and the spacer region rich in Proline and Alanine that link it to the rest of the protein. This result demonstrates that the stabilizer peptide (or derivative fragments from it) can be used advantageously as stabilizer peptides, due to the small influence that it would have on the immunogenicity of the polypeptides to which it is fused. This advantage is especially important if the fusion polypeptide constitutes a vaccine candidate.

Example 2

In order to express different heterologous proteins in *E. coli* through their fusion to the lipoic acid binding domain of the P64K antigen of *N. meningitidis* B:4:P1.15, the expression vector pM-83 was constructed, in which the sequence coding for a stabilizer peptide, derived from the first 47 amino acid of said protein was introduced (SEQUENCE IDENTIFICATION NUMBER: 1). This sequence is cloned under the control of the tryptophan promoter of *E. coil,* including the terminator of the bacteriophage T4 as signal for the transcription termination, and the ampicillin resistance gene as the selection marker.

To obtain the PM-83 expression vector, the stabilizer peptide was first amplified using the Polymerase Chain Reaction (PCR) (Randall, K. et al., Science, 42394, 487–491, 1988) from the plasmid pM-6, which carries the nucleotide sequence coding for the P64K antigen (European Patent application No. 0 474 313 A2, FIG. 1). For this purpose, the oligonucleotide primers 1573 and 1575 were used, which introduce NcoI and XbaI restriction sites in the amplified DNA fragment that correspond with the amino and carboxyl terminal ends of the stabilizer encoded by it:

NcoI

1573: 5' TTCCATGGTAGATAAAAG 3' (SEQUENCE IDENTIFICATION NUMBER: 2)

XbaI

1575: 5' TTTCTAGATCCAAAGTAA 3' (SEQUENCE IDENTIFICATION NUMBER: 3)

The amino acid sequence encoded by the resultant stabilizer is shown in FIG. 3 (SEQUENCE IDENTIFICATION NUMBER: 6). The introduction of the restriction site NcoI changes Leucine 2 for Valine; and the primer 1575 eliminates the sequence ETD (position 45–47), introducing in its place the sequence DLE. In this way the binding Lysine of the lipoic acid (position 48) does not form part of the stabilizer, and the vicinity of it, which is highly conserved in these domains (Russell, G. C., Guest, J. R., Biochim. Biophys. Record, 1076, 225–232, 1991) is altered. All this guarantees the elimination of the possibilities of posttranslational lipoylation of the fusion proteins that contain these domains, and the generation, during the immunization with these proteins, of auto antibodies of similar specificity to those present in the patients of primary biliary cirrhosis (Tuaillon, N., Andre, C., Briand, J. P. et al., J. Immunol., 148, 445–450, 1992).

Figure 4:
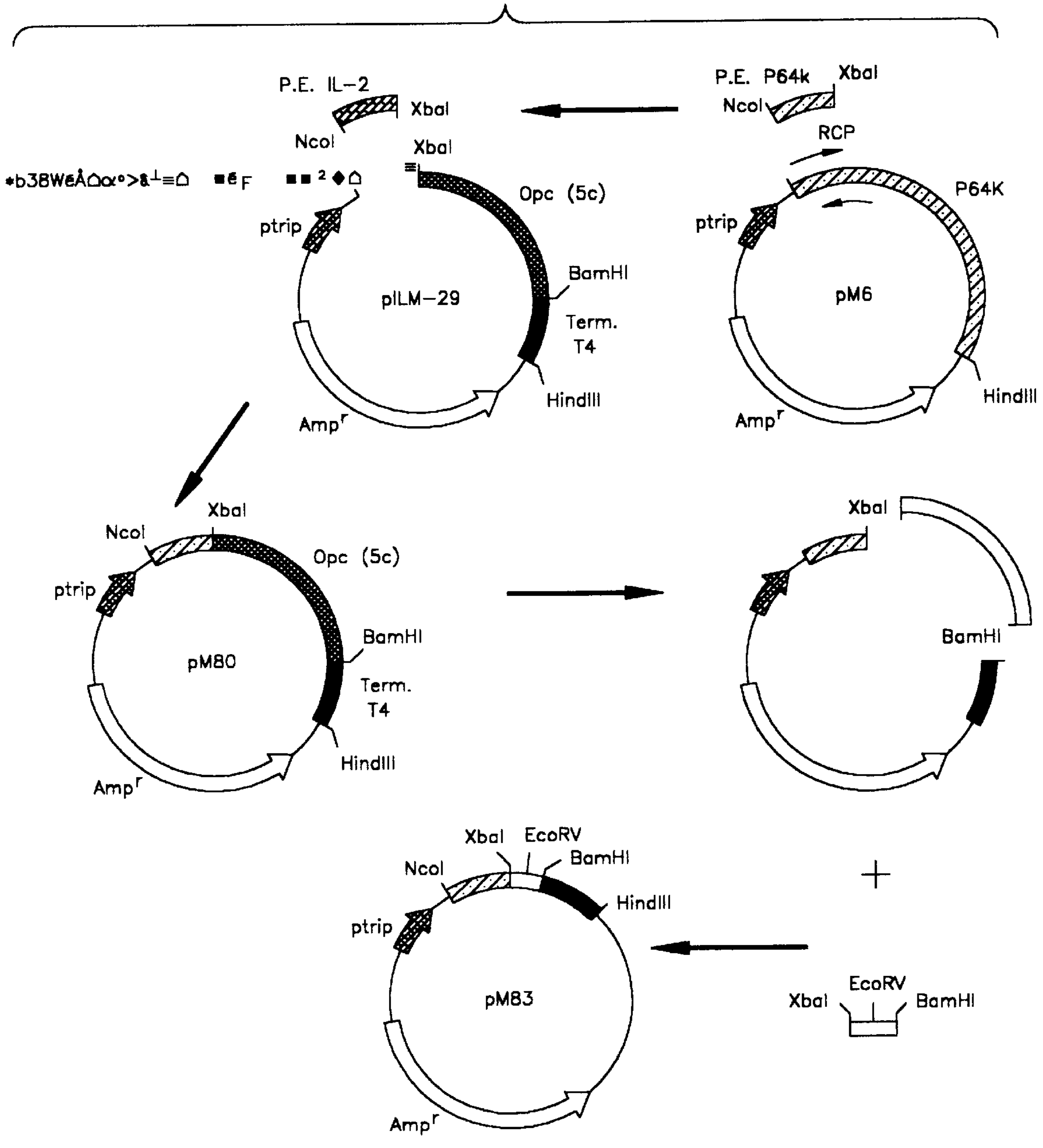
FIG. 4: Strategy for the construction of plasmid pM-83.

Plasmid pM-83 was constructed through the cloning of this fragment (SEQUENCE IDENTIFICATION NUMBER: 5) previously digested XbaI/NcoI in the plasmid pILM-29 (Guillen, G., Loyal, M., Alvarez, A. et al., Acta Biotecnologica, 15, 97–106, 1995). The pILM29 plasmid contains the gene for the protein Opc (5c) of *N. meningitidis* fused to a stabilizer peptide consistent in the first 58 amino acids with human IL-2, so that such cloning removes the fragment of IL-2 and fuses the Opc to the stabilizer of the P64K protein (FIG. 4). From the resultant plasmid, designated pM-80, the opc gene was excised using the enzymes XbaI and BamHI, and in its place was cloned an adapter formed by the hybridization of the oligonucleotides 1576 and 1577, which introduce restriction sites XbaI, EcoRV and BamHI in the extreme 3' of the stabilizer fragment:

1576 5' CTAGATTTGATATCAG 3' (SEQUENCE IDENTIFICATION NUMBER: 7)

1577 3' TAAACTATAGTCCTAG 5' (SEQUENCE IDENTIFICATION NUMBER: 8)

This plasmid was designated pM-83 (FIG. 4). The insertion of all the DNA fragments and oligonucleotides, as well as the maintenance of the correct reading frame, were verified by DNA sequencing according to Sanger, F. et al., (PNAS, USA, 74: 5463–5467, 1977).

Example 3

It is important that the stabilizer does not contain regions of high homology with human proteins if the resulting fusion protein is a vaccine candidate. The determination of the similarity of the stabilizer peptide of the pM-83 (EXAMPLE 2) with human proteins was accomplished through a search of homology in the data bases EMBL Data Library v.38 (Curl, C. M., Fuchs, R., Higgins, D. G. et al., Nucl. Acids Beast. 21, 2967–2971, 1993) of nucleotide sequences, and SWISS-PROT v.38 (Bairoch, A. and Boeckmann, B., Nucl. Acids Beast 21, 3093–3096, 1993) of amino acid sequences; both March 1994 versions. For this search two of the programs BLAST were used (Altschul, S. F., Gish, W., Miller, W., Myers, And. W. and Lipman, D. J., J. Mol. Biol., 215:403–410, 1990): BLASTP, that compares one amino acid sequence against a base of protein sequences (in this case SWISS-PROT) and TBLASTN, that compares an amino acid sequence against all the translations in both directions and in all the reading frames of a base of nucleotide sequences, as in this case the EMBL Data Library; in both cases it was used a valorization matrix PAM120 [Dayhoff, M. O., Schwartz, R. M. and Orcutt, B. B., in: Dayhoff, M. Or. (of.), Atlas of Protein Sequence and Structure, 5, supl.3, 345–352, Natn. Biomed. Beast. Found., Washington, 1978].

The result can be observed in FIGS. 5 and 6, in which the sheets of the respective results of the BLASTP and the TBLASTN are shown (homologous sequences of prokaryotes or inferior eukaryotes have been omitted for a better understanding). It is obvious that no human protein or proteins from any other mammal presents meaningful similarities with the stabilizer derived from the P64K; since the homologies detected by both algorithms (in the human and rat pyruvate kinases; and the C-terminal end of the human and canine mucines) present a highest casual occurrence probability (as a comparison point, the same probability, for the case of the dihydrolipoamide acetyltransferase of *Azotobacter vinelandii,* it is $3.7\times10^{-5}$).

Of all of the above mentioned it can be concluded that the use of said stabilizer in vaccine candidates is absolutely sure.

Example 4

The capacity of the present stabilizer in the pM-83 of permitting the intracellular synthesis at high levels and in the form of inclusion bodies was evaluated, comparing the expression of several proteins fused to the first 22 or 58 amino acids of the human Interleukin-2 (IL-2), a fusion peptide often used with this end, or fused to the first 47 a.a. of the P64K antigen modified according to is described in the EXAMPLE 2.

For this purpose the genes coding for the outer membrane proteins of *N. meningitidis* B:4:P1.15 PorA and Opc were cloned into the vectors pFP15 (hIL2-58; European Patent No. 416 673 B1) or pM-83 (P64K-47) ; and in the vectors pISL31 (hIL2-22, Castellanos-Sierra, L. R., Hardy, E., Ubieta, R., et al., paper submitted) or pM-83, the genes coding for a multiepitopic polypeptide (MEP) that includes immunogenic regions of several isolates of the Human Immunodeficiency Virus, HIV. The resultant expression plasmids are: pILM-28 (IL2-58 PorA; Guillén, G., Alvarez, A., Lion, L., et al., 494–498 in: Conde-González, C. J., Morse, S., Rice, P. et al. (eds) ., Pathobiology and Immunobiology of Neisseriaceae, Instituto de Salud Pública Nacional, Cuernavaca, Mexico, 1994), pM-82 (P64K-47 PorA; Niebla, O., Alvarez, A., González, S. et al., 85–86 in: Evans, J. S., Yost, S. and Maiden, M. C. J. et al. (eds.)., Neisseria 94: Proceedings of the IX International Pathogenic Neisseria Conference, Winchester, England, 1994), pILM-29 (IL2-58 Opc; Guillen, G., Leal, M., Alvarez, A. et al., Acta Biotecnológica, 15, 97–106, 1995), pM-80 (EXAMPLE 2, FIG. 4), pTAB4 (IL2-22+MEP) and pTAB9 (P64K-47 MEP).

The TAB4 and TAB9 proteins are multiepitopic polypeptides (MEP) that include several copies of the central part of the variable region 3 (V3) of the gp120 protein of the HIV-1. For the construction of these MEP, 15 central amino acids of the region V3 of the following isolates were selected:

LR150: SRGIRIGPGRAILAT (SEQUENCE IDENTIFICATION NUMBER: 9)

JY1: RQSTPIGLGQALYTT (SEQUENCE IDENTIFICATION NUMBER: 10)

RF: RKSITKGPGRVIYAT (SEQUENCE IDENTIFICATION NUMBER: 11)

MN: RKRIHIGPGRAFYTT (SEQUENCE IDENTIFICATION NUMBER: 12)

BRVA: RKRITMGPGRVYYTT (SEQUENCE IDENTIFICATION NUMBER: 13)

IIIB: SIRIQRGPGRAFVTI (SEQUENCE IDENTIFICATION NUMBER: 14)

Figure 7:
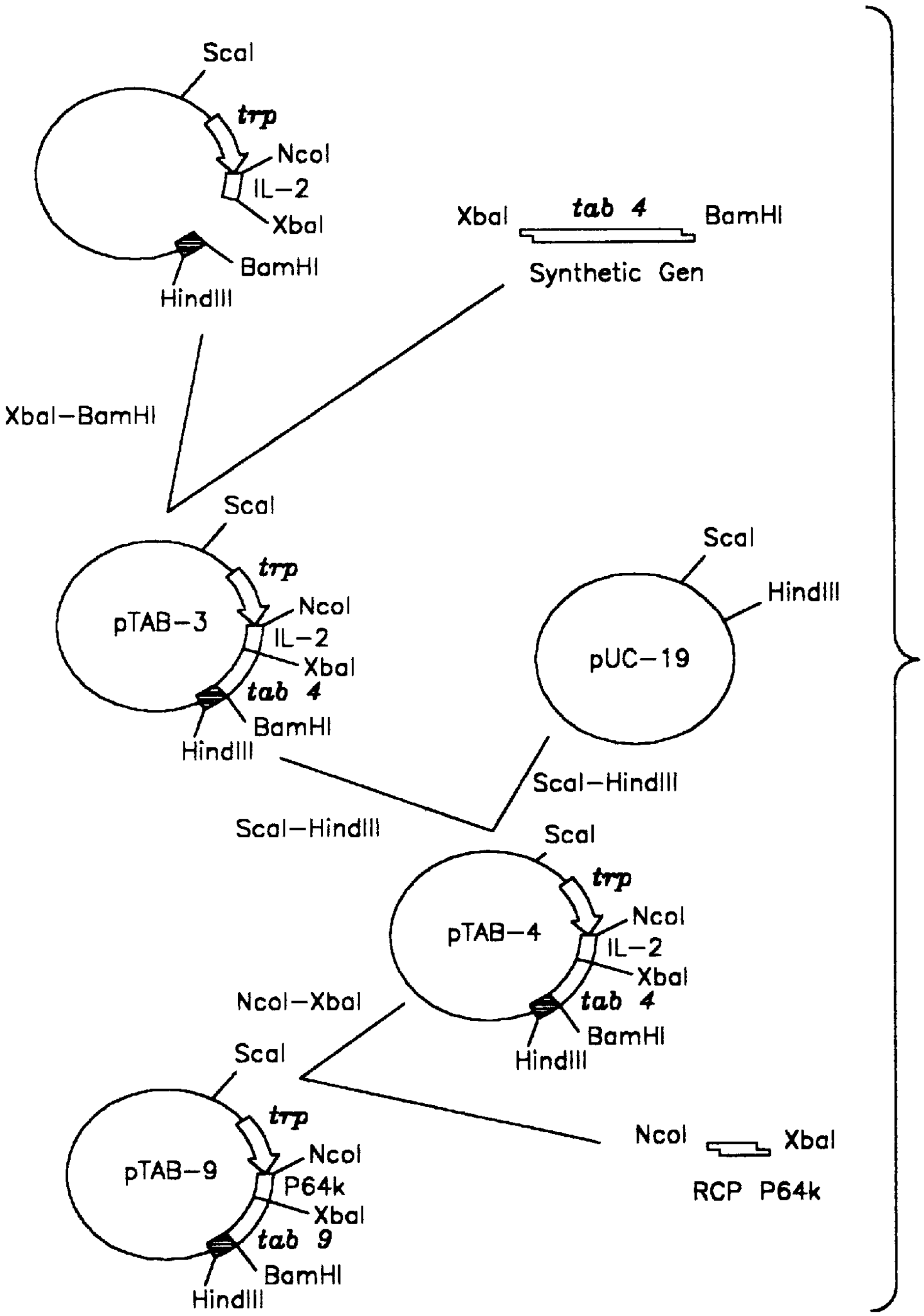
FIG. 7: Strategy for the construction of plasmids pTAB4 and pTAB9.
Figure 9A:
FIG. 9: A: General structure of the MEP TAB4 and TAB9. B: General structure of the MEP TAB13.

These regions are bound by a spacer peptide of five amino acids, of sequence AGGGA (SEQUENCE IDENTIFICATION NUMBER: 17). To achieve this, the DNA sequence coding for the V3 epitopes bound by the spacer peptide was obtained by chemical synthesis (SEQUENCE IDENTIFICATION NUMBER: 21) and was cloned under the control of the tryptophan promoter, fused to the first 22 amino acids of the human IL-2 (FIG. 7). From the resultant plasmid, designated pTAB3, a fragment containing the gene for the MEP, the tryptophan promoter and the T4 terminator was excised by digestion with the enzymes ScaI and HindIII, and is cloned into pUC19 (Yanisch-Perron, C. et al., 1985, Gene 33, 103–119) to obtain the pTAB4 (FIG. 7). Finally, the pTAB9 was constructed eliminating the sequence coding for the stabilizer derived from the human IL-2 by digestion with the enzymes NcoI and XbaI, and cloning, in its place, a fragment coding for the first 47 amino acids of the P64K antigen obtained by polymerase chain reaction (PCR), as is described in the EXAMPLE 2. The sequence of the resultant MEP is shown in FIG. 8, and its organization in FIG. 9A.

The host strains of *E. coli* K-12 used for all these plasmids were the W3110 (Hill, C. W., and Hamish, B, W. Proc. Natl. Acad. Sci., 78, 7069, 1981; Jensen, K. F., J. Bacteriol., 175, 3401–3407, 1993) for pILM-28, pILM-29, pM-80 and pM-82; and the W3110 trpA905, for pTAB4 and pTAB9. The expression was achieved in all the cases by inoculating a culture of 5 mL of LB medium (Sambrook, J., Fritsch, Y. F. and Maniatis, T., Molecular Cloning: To Manual Laboratory, Cold Spring Harbor Laboratory Press, 1989, New York, USA) with ampicillin (Ap) to 50 $^{\mu}$g/mL and tryptophan (W) to 100 $^{\mu}$g/mL, which was grown 12 h at 37° C. Said culture was used to inoculate a culture of 50 mL of LB-Ap (pTAB4 and pTAB9) or a defined medium compound by M9 salts (Miller, J. H., Experiments in Molecular Genetics, Cold Spring Harbor Laboratory Press, 1972, New York, USA), glucose to 1%, casein hydrolyzate to 1%, $CaCl_2$ 0.1 mM, $MgCl_2$ 1 mM and Ap to 50 ug/mL (pILM-28, pILM-29, pM-80, pM-82), those which were grown 12 h to 37° C. and 250 r.p.m. After this time, total protein samples were taken and analyzed by denatured polyacrylamide gel electrophoresis (SDS-PAGE, Laemmli, O. K., Nature, 277, 680, 1970s) and staining with Coomassie Brilliant Blue R-250. The expression percent was analyzed in a densiometre of laser Bromma-LKB. Their cellular location was determined by lysing the cells through treatment combined with lysozyme and ultrasound, after something then the soluble proteins were separated from the insoluble ones by centrifugation. The insolubility of the protein was used as criterion to assume its expression as inclusion bodies, since other conditions under which they can exhibit said behavior (association to membranes or to the peptide glycan) are unlikely in this case.

A summary of the results can be seen in the FIG. 10A. In all the cases the expression under the stabilizer derived from the P64K is comparable to the expression obtained when fused to peptides of the IL-2 concerning the relationship of heterologous protein: total cellular protein (see FIG. 10 B for the case of the MEP), which confirms the capacity of the pM-83 to be used as vector for the expression of fusion peptides. It is worth noting that these polypeptides are too hard to express in *E. coli* if they are not fused, either by their small size and sensitivity to proteases of the host, as the MEP, or by their toxicity in the case of the protein PorA and the bacterial porins in general (Carbonetti, N. H. and Sparling, P. F.; Proc. Natl. Acad. Sci. U.S.A., 84, 9084–9088, 1987). In all the cases the product was obtained as inclusion bodies, as is exemplified for the pTAB9 (FIG. 10C).

In conclusion, it is possible to outline that the use of the stabilizer derivative from the first 47 amino acids of the P64K antigen of *N. meningitidis* (P64K-47) results in an efficiency of expression of heterologous proteins as inclusion bodies, comparable to that of other systems (European patent applications No. 0 416 673 A2 and No. 229 998, Hoechst AG; European patent No. 0 416 673 B1; Castellanos-Sierra, L. R., Hardy, E., Ubieta, R., et al., manuscript submitted), with the additional benefit for the product of being used directly (i.e., without separating it from the stabilizer) due to the absence of meaningful homology with antigens of human origin.

Example 5

The availability of a ligand that recognizes specifically the stabilizer (e.g. an antibody, an enzymatic cofactor, etc.) is a desirable characteristic in any expression system of recombinant proteins. This is due so that the foregoing can permit, for instance, the design of efficient plans of affinity purification if said ligand is immobilize in a chromatographic resin; and even—in the case of the antibodies—the follow-up of the intermediate steps of the purification through immunologic techniques, independently of the identity of the expressed heterologous protein.

Figure 9B:
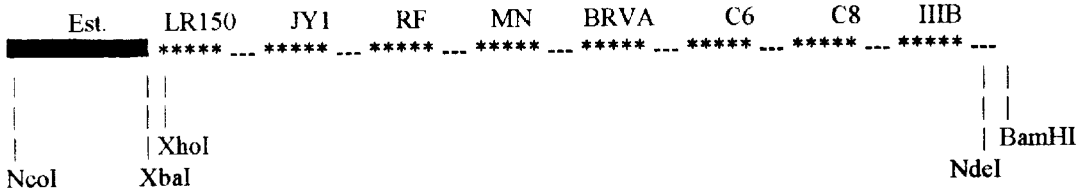

Such an objective was reached immunizing mice with the protein TAB13 (SEQUENCE IDENTIFICATION NO.: 20) in order to obtain monoclonal antibodies (MAb) against this stabilizer. TAB13 is an MEP derived from the TAB9 which is different from the former by the presence of two additional V3 consensus regions (FIG. 9B):

C6: TSITIGPGQVFYRTG (SEQUENCE IDENTIFICATION NO.: 15)
C8: RQRTSIGQGQALYTT (SEQUENCE IDENTIFICATION NO.: 16

This MEP was expressed (EXAMPLE 4) and purified (EXAMPLE 6) in an analogous way to that described for the TAB4 and TAB9.

Then, mice Balb/c were immunized by subcutaneous route with 3 doses of 20 $^{\mu}$g of TAB13 adsorbed to aluminum hydroxide adjuvant at a 15 days-interval. The animal were boosted by intraperitoneal route with 20 $^{\mu}$g of the same antigen in buffer phosphate, 20 days after the last dose. The splenocytes were fused with the myeloma X63 Ag8 653 and the resultant hybridomas were isolated and tested according to established methods (Gavilondo, J. V. (ed.), Monoclonal Antibodies: Theory and Practical, Elfos Scientiae, 1995, The Havana, Cuba).

The reactivity of the antibodies secreted by the isolated hybridomas was evaluated by ELISA, coating the plates with the MEP TAB13, the P64K protein or synthetic peptides representing the different V3 regions present in TAB13. In total 18 positive clones were obtained, one of which, designated 448/30/7, recognized TAB13 as well as 64K, but none of the peptides from the gp120.

The specificity of this MAb by the stabilizer peptide of the pM-83 and the possibility of its use for the immunologic detection of proteins that contain it, was determined by Western blotting, using different samples, heterologous proteins fused to the stabilizer derived from P64K (P64K-47), or the same fused protein or to the first 58 amino acids of the IL-2 (IL2-58). To do this, the *E. coli* strain MM294 was transformed (Sambrook, J., Fritsch, E. F. and Maniatis, T., Molecular Cloning: To Manual Laboratory, 1989, Cold Spring Harbor Laboratory Press, New York, USA) with the following plasmids: pILM-28 (IL2-58+porA), pM-82 (P64K-47+porA), pTAB13 (P64K-47+MEP), pM-6 (P64K) and pFP15 (IL-2). The expression plasmid pM-134 was also used, which contains the first 120 amino acids of the P64K, which includes the binding domain to the lipoic acid under the control of the same regulatory signals as in the previous plasmids. This segment was amplified by PCR using the primer 1573 (SEQUENCE IDENTIFICATION NO.: 2) and 2192 (SEQUENCE IDENTIFICATION NO.: 4); it was digested with the enzymes NcoI and BamHI, and was cloned in the plasmid pFP15 (see EXAMPLE 4) digested identically. The expression of these transformants was achieved in the growth conditions specified in the EXAMPLE 4 for the pTAB4 and the pTAB9.

The results obtained are represented in FIG. 11. As can be appreciated, MAb 448/30/7 recognizes a probably linear epitope within the stabilizer P64K-47, due to its reactivity with the samples of the plasmids pM-6, pM-82, pTAB13 and pM134 in spite of all these proteins being antigenically different. This experiment demonstrates that in no case is this reactivity due to the protein fused to the stabilizer (e.g. plasmids pILM-28 and pM-82: both carry the gene porA under different stabilizer) which evidences the specificity of recognition of this MAb.

In conclusion, the expression system formed by the stabilizer P64K-47, the plasmids that contain it and MAb 448/30/7 permit the efficient synthesis and in the form of inclusion bodies of a great variety of proteins, and their detection without the previous availability of immunologic probes against each polypeptide to express.

Example 6

The absence of deleterious effects on the immune response against the polypeptide fused to the stabilizer is an important factor to take into account upon selecting an expression system for vaccine candidates. One of the advantages of the expression system based on the stabilizer P64K-47 is precisely its decreased immunogenicity (EXAMPLE 1) which guarantees the foregoing. Nevertheless, the influence of the stabilizer P64K-47 in the immune response against the fused protein was evaluated qualitatively through the comparison of the antibodies response against the different peptides of the V3 region present in the MEP TAB4 (IL2-22) and TAB9 (P64K-47).

For the expression and the purification of TAB4 and TAB9, the biomass of the strain W3110 trpA905+pTAB4 and W3110 trpA905+pTAB9 was obtained as described in the EXAMPLE 4. This biomass was broken combining the treatment with lyzozyme and with ultrasound in fluoride presence of phenyl methyl sulfonyl (PMSF) and the non-ionic detergent Tritón-X-100; the inclusion bodies were obtained by differential centrifugation, and the MEP were partially purified and solubilized by two successive wash cycles of the inclusion bodies with chostropic agents and detergents (TAB4: 1. Urea 4 M Tritón-X-100 1%, 2. Urea 8 M. TAB9: 1. Urea 8 M Tritón-X-100 1%, 2. guanidium chloride 6 M). The supernatants obtained were finally purified through a gradient from 20 to 80% of acetonitrile in a column C4 VYDAC of high performance liquid chromatography (HPLC), being achieved 90% of purity approximately.

The purified recombinant proteins were adsorbed to a gel of aluminum hydroxide adjuvant using a relationship of 60 mg of adyuvant per mg of protein. These preparations were used to immunize 5 groups of rabbits by subcutaneous route with 200 $^{\mu}$g/dose. The immune response was evaluated by ELISA, using polystyrene plates of 96 wells (High binding, Costar, USA), well coated with the MEP used for the immunization, or with peptides corresponding to each one of the V3 regions present on it. The titers were calculated as the maximum dilution of each serum with an absorbance value of twice higher than that of a mixture of pre immune sera. All the sera were analyzed in duplicate.

What is claimed is:

1. A fusion protein which comprises a stabilizer peptide derived from the first 47 amino acids of the N-terminal end of the P64K antigen of *Neisseria meningitidis* B:4:P1.15 fused to a protein of viral origin.

2. The fusion protein according to claim 1 wherein the protein of viral origin is a multiepitopic polypeptide which comprises several copies of the central part of the variable region 3 (V3) from the gp 120 protein from HIV-1.

3. The fusion protein according to claim 2 wherein the multiepitopic polypeptide is TAB4, TAB9, or TAB4 and TAB9.

4. A method for producing a protein of viral origin as a fusion protein in *E. coli* wherein a peptide derived from the first 47 amino acids of the N-terminal end of the P64K antigen of *Neisseria meningitidis* B:4:P1.15 is used as a stabilizer for the expression of said protein of viral origin and a monoclonal antibody specific for the stabilizer is used for the immunodetection of said protein fused to it.

5. The method according to claim 4 wherein the amino acid sequence of the stabilizer peptide consists of the sequence of SEQ ID NO:6:

```
        10          20          30          40        47
MVDKRMALVE  LKVPDIGGHE  NVDIIAVEVN  VGDTIAVDDT  LITLDLE.
```

6. The method according to claim 4 wherein the monoclonal antibody used for the purification of the fusion protein is designated as 448/30/7.

7. The method according to claim 4 wherein the expressed protein of viral origin is any protein that could be employed as an immunogen in a vaccine preparation.

8. The method according to claim 4 wherein the expressed protein of viral origin is a multiepitopic polypeptide consisting of TAB4, TAB9, or TAB4 and TAB9.

9. A method of generating an immune response against a viral protein or a multiepitopic peptide comprising administering the fusion protein of claim 1, 2, or 3 in a vaccine preparation to humans or animals.

10. A vaccine which contains a fusion protein of claim 1, 2, or 3 as well as a suitable adjuvant.

11. A fusion protein which contains a stabilizer peptide derived from the first 47 amino acids of the N-terminal end of the P64K antigen of *Neisseria meningitidis* B:4:P1.15 fused to a protein of viral origin, wherein said stabilizer peptide consists of the amino acid sequence of SEQ ID NO:6:

\-

```
        10          20          30          40        47
MVDKRMALVE  LKVPDIGGHE  NVDIIAVEVN  VGDTIAVDDT  LITLDLE.
```

12. The fusion protein according to claim 11 wherein the protein of viral origin is a multiepitopic polypeptide which comprises several copies of the central part of the variable region 3 (V3) from the gp 120 protein from HIV-1.

13. The fusion protein according to claim 12 wherein the multiepitopic polypeptide is TAB4, TAB9, or TAB4 and TAB9.

* * * * *